(12) United States Patent
Takeuchi et al.

(10) Patent No.: US 7,995,093 B2
(45) Date of Patent: Aug. 9, 2011

(54) ENDOSCOPE APPARATUS

(75) Inventors: Shinji Takeuchi, Saitama (JP);
Kazunori Abe, Saitama (JP); Daisuke Ayame, Saitama (JP)

(73) Assignee: Fujinon Corporation, Saitama-shi (JP)

( * ) Notice: Subject to any disclaimer, the term of this patent is extended or adjusted under 35 U.S.C. 154(b) by 1371 days.

(21) Appl. No.: 11/355,983

(22) Filed: Feb. 17, 2006

(65) Prior Publication Data
US 2006/0197830 A1 Sep. 7, 2006

(30) Foreign Application Priority Data
Mar. 4, 2005 (JP) ................ P.2005-060198

(51) Int. Cl.
*A62B 1/04* (2006.01)
*H04N 13/00* (2006.01)
*H04N 3/14* (2006.01)
*H04N 5/76* (2006.01)
*H04N 5/222* (2006.01)

(52) U.S. Cl. ......... 348/65; 348/45; 348/273; 348/231.6; 348/370

(58) Field of Classification Search .............. 348/71, 348/72, 45, 68, 273, 65, 231.3, 231.6, 370
See application file for complete search history.

(56) References Cited

U.S. PATENT DOCUMENTS

| | | | |
|---|---|---|---|
| 4,885,634 A | 12/1989 | Yabe | |
| 5,408,263 A | 4/1995 | Kikuchi et al. | |
| 6,295,082 B1 * | 9/2001 | Dowdy et al. | 348/72 |
| 7,172,553 B2 * | 2/2007 | Ueno et al. | 600/160 |
| 7,542,069 B2 * | 6/2009 | Tashiro | 348/72 |
| 7,800,656 B2 * | 9/2010 | Takeuchi et al. | 348/65 |
| 2002/0175993 A1 * | 11/2002 | Ueno et al. | 348/65 |
| 2003/0001952 A1 | 1/2003 | Iida et al. | |
| 2003/0179291 A1 | 9/2003 | Kobayashi et al. | |
| 2004/0141054 A1 | 7/2004 | Mochida et al. | |

FOREIGN PATENT DOCUMENTS

| | | |
|---|---|---|
| EP | 1 302 152 A1 | 4/2003 |
| JP | 63-240826 A | 10/1988 |
| JP | 6-90900 A | 4/1994 |
| JP | 2003-93336 A | 4/2003 |

* cited by examiner

*Primary Examiner* — Nhan T Tran
(74) *Attorney, Agent, or Firm* — Birch, Stewart, Kolasch & Birch, LLP

(57) ABSTRACT

In an endoscope apparatus in which a scope is connected to a processor unit in a freely attachable and detachable way, the endoscope apparatus wherein matrix calculation is conducted for RGB signals formed by using CCD, a color space conversion processing circuit is provided for forming spectral images of the arbitrarily selected wavelength range. CCD characteristics identification information including types of color filters of the CCD and spectral characteristics or scope characteristics information is stored in the ROM of the scope, a plurality of matrix data corresponding to characteristics identification information is stored in the memory of the processor unit, and matrix data corresponding to the obtained characteristics information is read from the memory, thereby forming an excellent spectral image by using data suitable for characteristics of the CCD or the scope.

2 Claims, 4 Drawing Sheets

FIG. 2A

| SCOPE CHARACTERISTICS IDENTIFICATION INFORMATION | CCD CHARACTERISTICS | IDENTIFICATION INFORMATION | LIGHT SOURCE | LIGHT GUIDE AND OTHERS |
|---|---|---|---|---|
| A | COMPLEMENTARY COLOR TYPE+$I_1$ | $C_1$ | XENON | $q_1$ |
| B | COMPLEMENTARY COLOR TYPE+$I_2$ | $C_2$ | HALOGEN | $q_2$ |
| C | COMPLEMENTARY COLOR TYPE+$I_3$ | $C_3$ | XENON | $q_3$ |
| D | ELEMENTARY COLOR TYPE+$I_4$ | $C_4$ | XENON | $q_4$ |
| | ($I_1, I_2, I_3, I_4\cdots$: SPECTRAL CHARACTERISTICS) | | | |
| ⋮ | ⋮ | ⋮ | ⋮ | ⋮ |

FIG. 2B

| SCOPE CHARACTERISTICS IDENTIFICATION INFORMATION | MATRIX DATA |
|---|---|
| A | $P_{a1}$ |
| B | $P_{a2}$ |
| C | $P_{a3}$ |
| D | $P_{a4}$ |
| ⋮ | ⋮ |

FIG. 2C

| CCD CHARACTERISTICS IDENTIFICATION INFORMATION | MATRIX DATA |
|---|---|
| $C_1$ | $P_{b1}$ |
| $C_2$ | $P_{b2}$ |
| $C_3$ | $P_{b3}$ |
| $C_4$ | $P_{b4}$ |
| ⋮ | ⋮ |

ENDOSCOPE APPARATUS

BACKGROUND OF THE INVENTION

1. Field of the Invention

The present invention relates to an endoscope apparatus, more particularly, a constitution used in medical fields for forming and displaying a spectral image (video) made up of image information of arbitrarily selected wavelength ranges.

2. Description of the Related Art

Recently, in a electronic endoscope apparatus which uses a solid imaging device, spectral imaging combined with a narrow bandpass filter on the basis of a spectral reflectance in alimentary canal (gastric mucosa and the like), namely, a narrow band filter built-in an electronic endoscope apparatus (Narrow Band Imaging-NBI) has become the focus of attention. In place of rotational filters of R (red), G (green) and B (blue) by a frame sequential method, this system is provided with band pass filters of three narrow bands (wavelengths), outputs sequentially illumination light via these narrow bandpass filters, and conducts processing the same as in the case of red (R), green (G) and blue (B) signals while changing respective weightings to three signals obtained from these illumination lights, thereby forming a spectral image. This spectral image is able to realize micro-structures and the like in gastrointestinal tracts such as the stomach and large-intestine, which would otherwise not be realized.

In contrast, unlike the frame sequential method using the above-described narrow bandpass filters, as described in Japanese Published Unexamined Patent Application No. 2003-93336, it has been proposed that in the simultaneous method in which micro-mosaic color filters are arranged on a solid imaging device, a spectral image is formed by the computing process on the basis of image signals obtained from white light. In this method, the relationship between numeric data of the respective R, G, and B color sensitivity characteristics and numeric data of spectral characteristics of a specific narrow bandpass is determined as matrix data (coefficient sets) and computing is made for the matrix data and the R, G and B signals to obtain spectral image signals artificially via the narrow band pass filters. Where a spectral image is formed by such computing, it is not necessary to provide a plurality of filters corresponding to desired wavelength ranges and to provide these change-over arrangements, thereby successfully avoiding increases in the size of a system and reducing cost.

However, endoscope apparatuses in which different types of endoscopes (scope) are connected to a single processor unit have been recently used, and user-friendly endoscope apparatuses have been demanded in view of such circumstances.

Further, in the computing processing of spectral images in the endoscope apparatus, such a problem has been brought about that underlying RGB color image signals are different depending on types of color filters of an imaging device (solid imaging device and others), spectral sensitivity characteristics, types of light sources and spectral sensitivity characteristics of optical system components of an endoscope such as a light guide, and the constitutions of a endoscope or light source influence formation of a spectral image, resulting in a difference in reproducibility in the same wavelength range. More specifically, a CCD, and a solid imaging device, includes a complementary color-type CCD having color filters of Mg, Ye, Cy and G and an elementary color-type CCD having RGB color filters, different in spectral sensitivity characteristics according to individual differences. FIG. 5 shows an example of spectral sensitivity characteristics of color filters of a complementary color type CCD. The color filters Mg, Ye, Cy and G, differ in spectral sensitivity according to individual differences in CCD. In the computing processing employing single matrix data, such difference in spectral characteristics is reflected in the computing result, thereby influencing formation of a spectral image.

SUMMARY OF THE INVENTION

The present invention has been made in view of the above problem, and an object of the invention is to provide a user-friendly endoscope apparatus capable of forming a spectral image excellent in reproducibility in the same wavelength range, even where characteristics of an imaging device or an endoscope and types of light sources differ.

In order to attain the above object, an endoscope apparatus according to the first aspect of the invention comprises: an endoscope comprising an imaging device that forms color image signals of a body to be observed; and a processor unit comprising an image signal processing circuit, wherein the endoscope is connected to the processor unit in a freely attachable and detachable way, the apparatus comprising: a spectral image forming circuit that conducts matrix calculation based on a color image signal obtained by the imaging device and forms a spectral image of an arbitrarily selected wavelength range, the spectral image forming circuit being arranged on the processor unit; a characteristics information retaining/generating portion having endoscopic characteristics identification information influencing formation of the spectral image, wherein the endoscopic characteristics identification information includes information on at least one of types of color filters of the imaging device and spectral characteristics of the color filters, the characteristics information retaining/generating portion being arranged on the endoscope; a characteristics information obtaining portion that obtains the endoscopic characteristics identification information at the characteristics information generating portion, the characteristics information obtaining portion being arranged on the processor unit; a storage portion that stores a plurality of matrix data for forming a spectral image corresponding to the endoscopic characteristics identification information; and a control portion that reads corresponding matrix data from the storage portion based on the endoscopic characteristics identification information obtained at the characteristics information obtaining portion and allows the spectral image forming circuit to conduct matrix calculation according to the read matrix calculation data.

An endoscope apparatus according to the second aspect of the invention, wherein the characteristics information obtaining portion obtains information on types of light sources for emitting light illumination from the endoscope end part and selects matrix data according to a type of the light source.

According to the above-described constitution, for example, characteristics information on types of color filters of an imaging device or spectral characteristics or characteristics information on an endoscope (scope) in which characteristics of optical system components such as a light guide are added to characteristics of the imaging device is stored as a characteristics information retaining/generating portion. A plurality of matrix data (coefficient sets) previously prepared in accordance with the above characteristics information is also stored in the computing memory of the processor unit. When the endoscope is connected, the microcomputer of the processor unit receives characteristics information of the imaging device or characteristics information on the endoscope through communications with the microcomputer of the endoscope, reads from the memory matrix data suitable for the characteristics information and supplies the data to the spectral image forming circuit. Therefore, matrix calculation is conducted for forming a spectral image in combination with wavelength ranges (narrow bands) selected by the above-described corresponding matrix data and RGB signals in the spectral image forming circuit.

In the constitution of the second aspect, matrix data is stored which is prepared by adding to the characteristics information the information on the use of a xenon lamp or a halogen lamp as a light source. The processor unit recognizes and judges a type of light source, thereby forming a spectral image by using matrix data which corresponds not only to characteristics of the imaging device or the endoscope but also to the characteristics information on the light source.

BRIEF DESCRIPTION OF THE DRAWINGS

FIG. 2A is a view showing characteristics of the scope and CCD in the embodiment and identification information;

FIGS. 2B and 2C are views showing matrix data selected in accordance with the identification information;

DETAILED DESCRIPTION OF THE INVENTION

Figure 1:
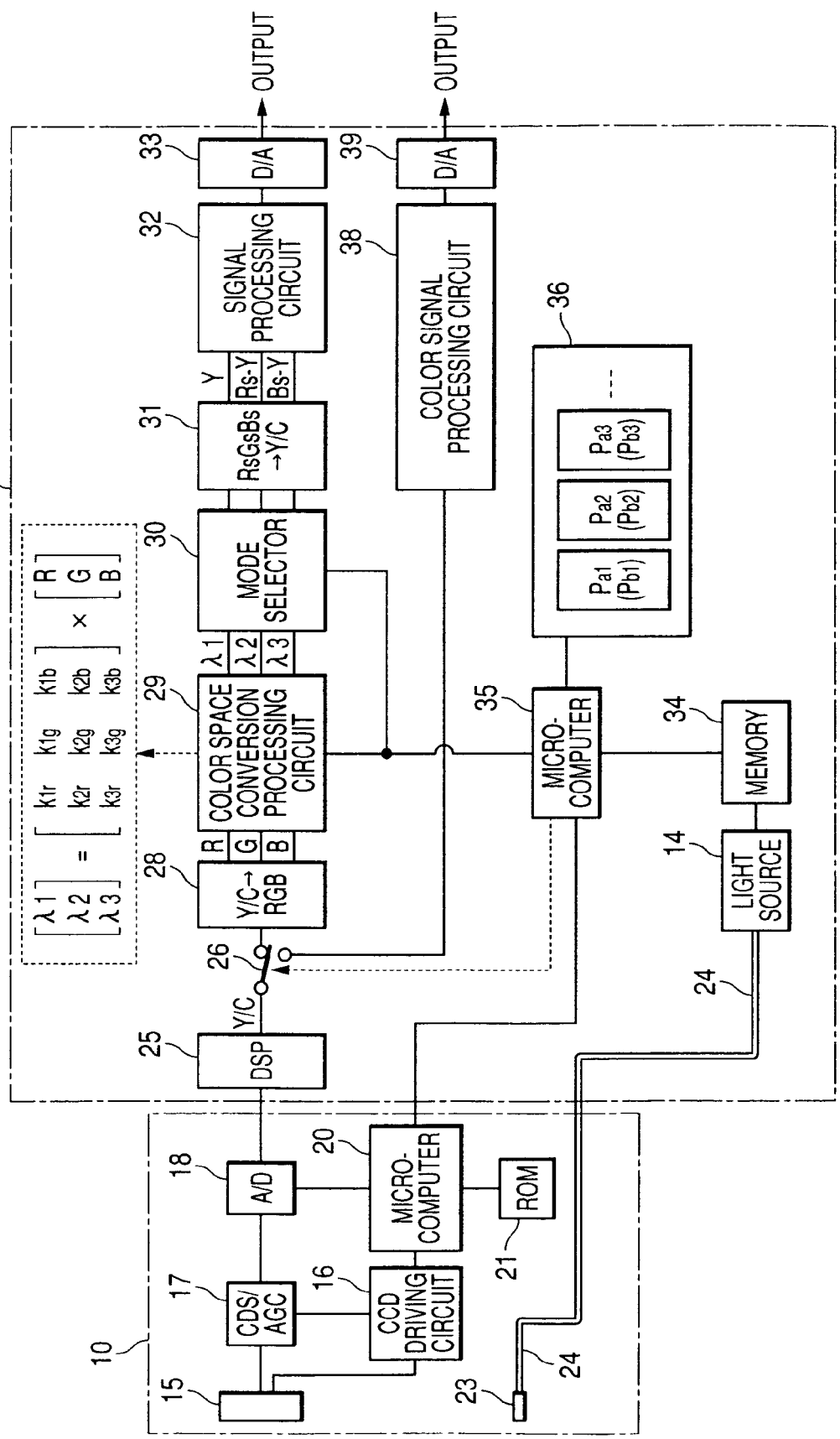
FIG. 1 is a block diagram showing the constitution of an endoscope apparatus of an embodiment in the present invention.

FIG. 1 shows a constitution of the electronic endoscope apparatus of the embodiment. As shown in FIG. 1, the electronic endoscope apparatus is constituted so that a scope (electronic endoscope) 10 is connected to a processor unit 12 in a freely attachable and detachable way and a light source 14 is arranged on the processor unit 12. Further, the light source 14 may be arranged on a light source unit, which is a separate body. The scope 10 is provided on the end part with a CCD 15 which is a solid imaging device, and either a complementary color-type CCD having color filters of Mg, Ye, Cy and G or an elementary color-type CCD having RGB color filters on an imaging surface is used as the CCD 15.

The CCD 15 is provided with a CCD driving circuit 16 for forming a driving pulse on the basis of synchronizing signals, a CDS/AGC (correlated dual sampling/automatic gain control) circuit 17 for sampling and amplifying an image (video) signal input from the CCD 15 the image signal and an A/D converter 18. Also provided are a microcomputer 20 and a memory (ROM) 21 (corresponding to the characteristics information retaining/generating portion) for controlling various circuits inside the scope 10 and controlling communications with the processor unit 12. Characteristics identification information ($C_1$, $C_2$, $C_3$, $C_4$ . . . ) on the type of color filters of the CCD 15 (complementary color-type CCD or elementary color-type CCD) and spectral characteristics or characteristics identification information (A, B, C, D . . . ) on the scope 10 in which characteristics of optical system components such as a light guide (24) to be described later are added to characteristics of the CCD 15 is stored in the memory 21. Further, the scope 10 is provided at the distal end with an illumination window 23, and the illumination window 23 is connected to the light source 14 by a light guide 24.

The processor unit 12 is provided with a DSP (digital signal processor) 25 which imparts a variety of image processings to digitally converted image signals. In the DSP 25, a brightness (Y) signal and a color difference [C(R-Y,B-Y)] signal are output by an internal color conversion circuit, irrespective of whether the above CCD 15 is a complementary color type or an elementary color type. The DSP 25 is provided with a first color conversion circuit 28 via a selector 26 (at the other end). In the first color conversion circuit 28, the Y (brightness)/C (color difference) signals output from the DSP 25 are converted to RGB signals. Further, the DSP 25 may be arranged on the scope 10.

At the post-stage of the first color conversion circuit 28, a color space conversion processing circuit 29 (corresponding to the spectral image forming circuit) for conducting matrix calculation for a spectral image and outputting spectral image signals of the selected wavelength, $\lambda 1$, $\lambda 2$ or $\lambda 3$, a mode selector 30 for selecting either spectral images made up of one wavelength range (narrow band) (monochrome mode) or spectral images made up of three wavelength ranges (3-colormode), a second color conversion circuit 31 for inputting image signals ($\lambda 1$, $\lambda 2$ and $\lambda 3$) in one wavelength range or three wavelength ranges as Rs, Gs and Bs signals in order to carry out a processing which corresponds to conventional RGB signals and a signal processing circuit 32 for conducting a variety of other signal processings (mirror image process, mask generation, character generation and the like) and D/A converter 33.

A microcomputer 35 (corresponding to the characteristics information obtaining portion and the control portion) is also provided, which controls respective circuits inside the processor unit 12, reads corresponding matrix data from a memory 36 (corresponding to the storage portion) on the basis of the endoscopic characteristics identification information obtained through communications with the scope 10 and supplies the data to the color space conversion processing circuit 29. A plurality of matrix data (table) on $P_{a1}$, $P_{a2}$, $P_{a3}$ . . . or $P_{b1}$, $P_{b2}$, $P_{b3}$ . . . which corresponds to the above characteristics identification information on A,B,C,D . . . or $C_1, C_2, C_3, C_4$ . . . are stored in the memory 36.

Tables 1 and 2 below show respective examples of the matrix data used in forming spectral images of the embodiment and accommodated in the memory 36. Table 1 and Table 2 respectively show an example in which the complementary color type CCD 15 is used and an example in which the elementary color type CCD 15 is used, each of which corresponds to the characteristics identification information of the scope 10.

TABLE 1

| Parameter | $k_{pr}$ | $k_{pg}$ | $k_{pb}$ |
|---|---|---|---|
| p1 | 0.000006 | −0.0004 | 0.002803 |
| p2 | −0.00014 | −0.0004 | 0.003323 |
| p3 | −0.00029 | −0.00032 | 0.003698 |
| p4 | −0.00039 | −0.00027 | 0.00394 |
| p5 | −0.00048 | −0.00021 | 0.004093 |
| p6 | −0.00057 | −0.00015 | 0.004175 |
| p7 | −0.00065 | −9.4E−05 | 0.004241 |
| p8 | −0.00075 | −2.7E−05 | 0.004301 |
| p9 | −0.00086 | 0.00005 | 0.004364 |
| p10 | −0.00097 | 0.000147 | 0.004412 |
| p11 | −0.00109 | 0.000284 | 0.004418 |
| p12 | −0.00121 | 0.000462 | 0.004374 |
| . | . | . | . |
| . | . | . | . |

TABLE 1-continued

| Parameter | $k_{pr}$ | $k_{pg}$ | $k_{pb}$ |
|---|---|---|---|
| . | . | . | . |
| p25 | −0.00224 | 0.006386 | −0.00049 |
| p26 | −0.00218 | 0.006796 | −0.00098 |
| p27 | −0.00204 | 0.007045 | −0.00138 |
| p28 | −0.00183 | 0.007155 | −0.00172 |
| p29 | −0.00156 | 0.007164 | −0.00201 |
| p30 | −0.00126 | 0.007064 | −0.00221 |
| . | . | . | . |
| . | . | . | . |
| p61 | 0.008058 | −0.00226 | −0.00104 |

TABLE 2

| Parameter | $k_{pr}$ | $k_{pg}$ | $k_{pb}$ |
|---|---|---|---|
| p1 | 0.000083 | −0.00188 | 0.003592 |
| p2 | −0.00027 | −0.0022 | 0.004251 |
| p3 | −3.4E−05 | −0.00239 | 0.004728 |
| p4 | −8.2E−05 | −0.0025 | 0.005033 |
| p5 | −0.00013 | −0.00256 | 0.00522 |
| p6 | −0.00019 | −0.00253 | 0.005296 |
| p7 | −0.00027 | −0.00248 | 0.005345 |
| p8 | −0.00035 | −0.00241 | 0.005379 |
| p9 | −0.00045 | −0.00232 | 0.005409 |
| p10 | −0.00055 | −0.00221 | 0.005422 |
| p11 | −0.00065 | −0.00205 | 0.005381 |
| p12 | −0.00074 | −0.00185 | 0.00528 |
| . | . | . | . |
| . | . | . | . |
| p25 | −0.00118 | 0.004966 | −0.00096 |
| p26 | −0.00114 | 0.005514 | −0.00156 |
| p27 | −0.00105 | 0.005901 | −0.00204 |
| p28 | −0.00092 | 0.006144 | −0.00242 |
| p29 | −0.00075 | 0.00628 | −0.00273 |
| p30 | −0.00057 | 0.006287 | −0.00292 |
| . | . | . | . |
| . | . | . | . |
| p61 | 0.00548 | −0.00229 | 0.00453 |

Matrix data given in the above Table 1 and Table 2 are made up of 61-wavelength range parameters (coefficient sets) p1 to p61 in which, for example, the wavelength range of 400 nm to 700 nm is divided into 5 nm intervals. The parameters p1-p61 are constituted by coefficients, $k_{pr}$, $k_{pg}$ and $k_{pb}$ (p corresponds to p1-p61) for matrix calculation.

Then, in the color space conversion processing circuit 29, matrix calculation is conducted according to the following mathematical formula 1 represented by the coefficients $k_{pr}$, $k_{pg}$ and $k_{pb}$, and RGB signals output from the first color conversion circuit 28.

[Mathematical Formula 1]

$$\begin{bmatrix} \lambda 1 \\ \lambda 2 \\ \lambda 3 \end{bmatrix} = \begin{bmatrix} k1r & k1g & k1b \\ k2r & k2g & k2b \\ k3r & k3g & k3b \end{bmatrix} \times \begin{bmatrix} R \\ G \\ B \end{bmatrix}$$ [Mathematical Formula 1]

More specifically, where, for example, the parameter p4 (center wavelength 415 nm), p6 (center wavelength 425 nm) and p9 (center wavelength 440 nm) in Table 1 are selected as λ1, λ2 and λ3, (−0.00039, −0.00027, 0.00394) of p4, (−0.00057, −0.00015, 0.004175) of p6 and (−0.00086, 0.00005, 0.004364) of p9 may be substituted as coefficients ($k_{pr}$, $k_{pg}$ and $k_{pb}$).

Further, a color signal processing circuit 38 for forming ordinary color images (videos) not for spectral images and a D/A converter 39 are connected and arranged for the other terminal of the selector 26.

The embodiment is constituted as described above. As shown in FIG. 1, when the scope 10 is connected to the processor unit 12, the microcomputer 35 of the processor unit 12 performs communications with the microcomputer 20 of the scope 10 to obtain the scope characteristics identification information or CCD identification information, thereby selecting matrix data corresponding to the above information and reading the data from the memory 36.

FIG. 2 shows the scope of the embodiment or CCD characteristics and identification information [FIG. 2A] as well as matrix data selected in accordance with the identification information [FIG. 2B and FIG. 2C]. For example, as shown in FIG. 2A, in an A-type scope 10, the identification information is A, the color filter is of a complementary color type, CCD 15 of the identification information $C_1$ having the spectral characteristics 11 is loaded, a xenon lamp is used as a light source 14, and other spectral characteristics such as a light guide are q1. In a B type scope 10, the identification information is B, the color filter is of a complementary color type, CCD 15 of the identification information $C_2$ having the spectral characteristics 12 is loaded, a halogen lamp is used as a light source 14 and other spectral characteristics such as a light guide are q2. Further, information on the type of light source 14 is retained in the memory 34 and others, and the information is referred to by the microcomputer 35 of the processor unit 12.

When making matrix data correspond to the scope characteristics identification information, as shown in FIG. 2B, matrix data of Pa1, Pa2, Pa3, Pa4 . . . (those shown in Table 1 and Table 2) is selected sequentially in accordance with identification information A, B, C, D . . . , the matrix data is read from the memory 36 and supplied to the color space conversion processing circuit 29. Further, when making matrix data correspond to the CCD characteristics identification information, as shown in FIG. 2C, matrix data of Pb1, Pb2, Pb3, Pb4 . . . is selected sequentially in accordance with identification information $C_1$, $C_2$, $C_3$, $C_4$ . . . and the matrix data is supplied to the color space conversion processing circuit 29.

In the color space conversion processing circuit 29, in order to form a spectral image, matrix calculation is conducted according to the above mathematical formula 1. Where, for example, matrix data of Table 1 is selected and p3 (center wavelength 410 nm), p10 (center wavelength 445 nm) and p26 (center wavelength 525 nm) are selected as three wavelength ranges (λ1, λ2 and λ3), signals of λ1, λ2 and λ3 are determined according to matrix calculation of the following mathematical formula 2 represented by RGB signals.

[Mathematical Formula 2]

$$\begin{bmatrix} \lambda 1 \\ \lambda 2 \\ \lambda 3 \end{bmatrix} = \begin{bmatrix} -0.00029 & -0.00032 & 0.003698 \\ -0.00097 & 0.000147 & 0.004412 \\ -0.00218 & 0.006796 & -0.00098 \end{bmatrix} \times \begin{bmatrix} R \\ G \\ B \end{bmatrix}$$ [Mathematical Formula 2]

Then, where a three-color mode is selected by the mode selector 30, the above signals λ1, λ2 and λ3 are supplied to the second color conversion circuit 31 as signals of Rs (=λ1), Gs (=λ2) and Bs (=λ3). Where a monochrome mode is selected, any one of the above signals λ1, λ2 and λ3 is supplied to the second color conversion circuit 31 as the signal Rs (=λ2), Gs (=λ2) or Bs (=λ2) (for example, λ2 is selected). In the second color conversion circuit 31, signals Rs (=λ2), Gs (=λ2) and Bs (=λ2) are converted to Y/C signals (Y, Rs-Y and Bs-Y), and the Y/C signals are supplied to the monitor via the signal processing circuit 32 and the D/A converter 33.

Figure 3:
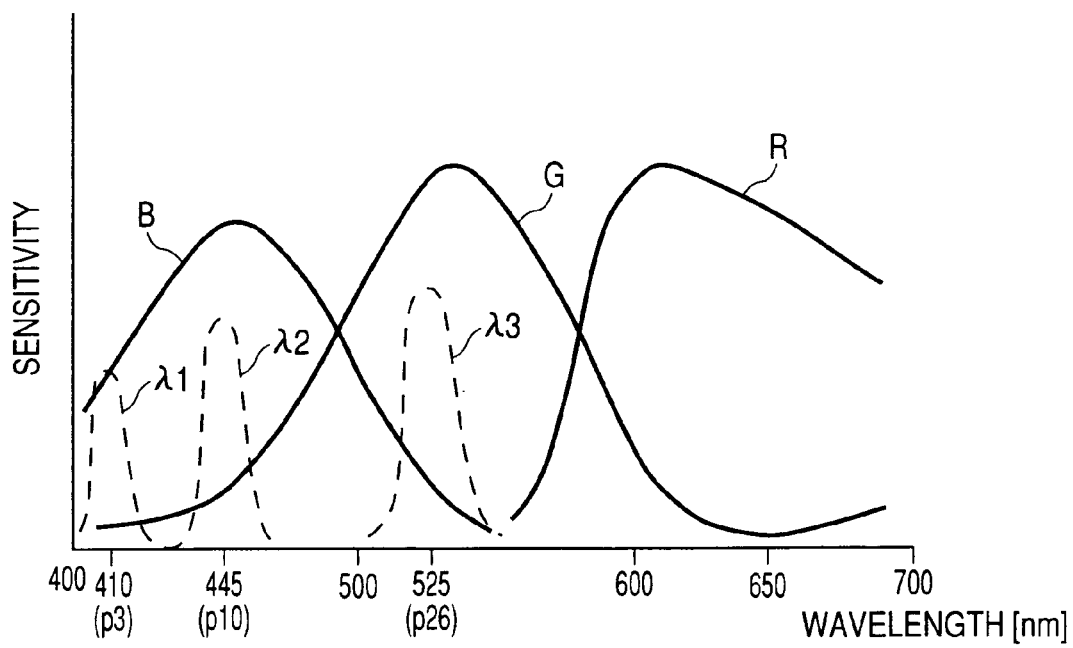
FIG. 3 is a graph showing one example of the wavelength range of spectral images formed in the embodiment, together with spectral sensitivity characteristics of the elementary color-type CCD.
Figure 4:
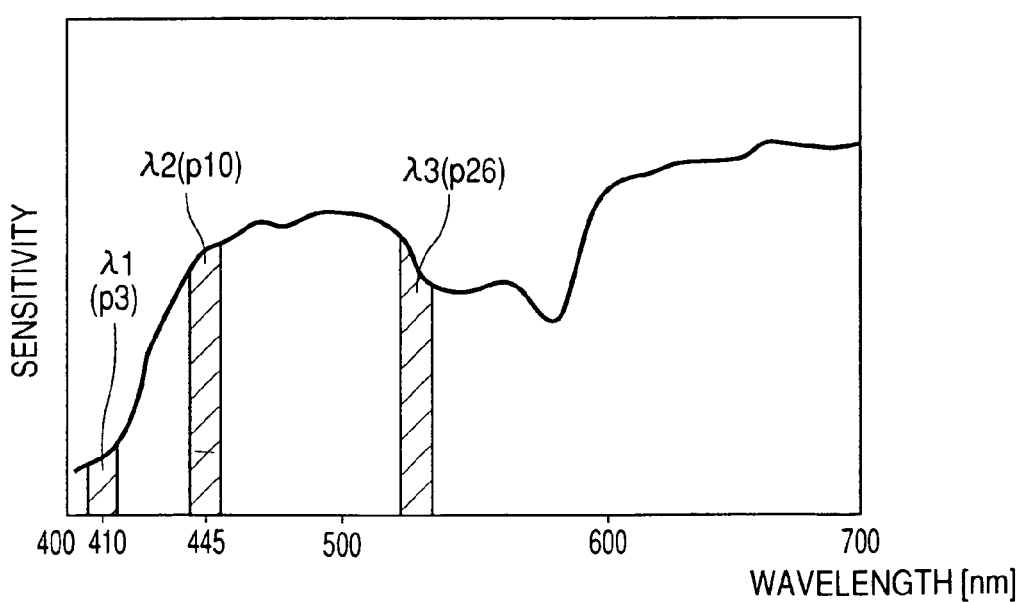
FIG. 4 is a graph showing one example of the wavelength range of spectral images formed in the embodiment, together with the reflection spectrum of a living body.
Figure 5:
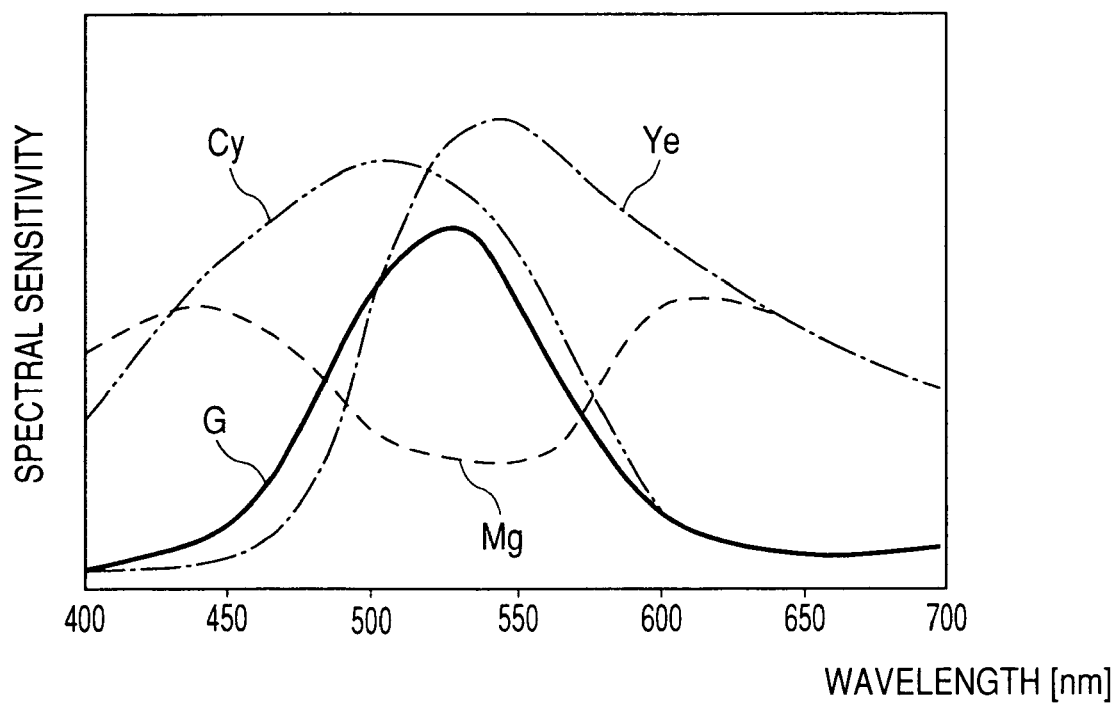
FIG. 5 is a graph showing one example of the spectral sensitivity characteristics of a complementary color-type CCD.

As described above, spectral images displayed on a monitor and others are constituted by color components of the wavelength ranges shown in FIG. 3 and FIG. 4. More specifically, FIG. 3 is a conceptual diagram in which three wavelength ranges forming spectral images are superimposed on spectral sensitivity characteristics of color filters on the CCD 15 (elementary color type) (the color filter is not in agreement with the sensitivity graduation of wavelength ranges corresponding to λ1, λ2 and λ3 signals). Further, FIG. 4 is a conceptual diagram in which three wavelength ranges are superimposed on the reflection spectrum of a living body. The wavelengths p3, p10 and p26 selected as λ1, λ2 and λ3 signals in the embodiment are color signals having a wavelength range of approximately ±10 nm, with the center wavelength being 410 nm, 445 nm and 525 nm in sequence, as shown in the diagram, then, spectral images (moving image and still image) constituted by a combination of colors of three wavelength ranges are displayed. Further, where an ordinary color image is formed, the selector 26 is changed by the microcomputer 35, thereby making it possible to display on a monitor and other color images (moving image and still image) similar to conventional images.

In the above embodiment, information on the type (characteristics) of the light source 14 is retained in the processor unit 12. Where a light source unit is separately connected for use, the information on the type of light source 14 will be obtained by communications with the light source unit. It may also be constituted in such a way that the scope characteristics identification information, the CCD characteristics identification information and the light source characteristics identification information are recognized not by communications between microcomputers but by access to a predetermined component circuit inside the scope 10, analysis of image signals obtained in the CCD 15 and judgment of identification shape members arranged on the connector joints such as circuits upon connection.

With the endoscope apparatus of the present invention, a spectral image excellent in reproducibility in the same wavelength range can be formed even where there is a difference in characteristics of an imaging device or an endoscope or in the type of light sources, and an excellent spectral image can be obtained where different types of endoscopes are connected to a single processor unit, thus making it possible to provide a user-friendly endoscope apparatus.

Further, according to the second aspect of the invention, it is advantageous in that a spectral image excellent in reproducibility can be formed even where a different light source is used.

The entire disclosure of each and every foreign patent application from which the benefit of foreign priority has been claimed in the present application is incorporated herein by reference, as if fully set forth.

What is claimed is:

1. An endoscope apparatus comprising:
    an endoscope comprising an imaging device that forms color image signals of a body to be observed; and
    a processor unit comprising an image signal processing circuit, wherein the endoscope is connected to the processor unit in a freely attachable and detachable way,
    the apparatus comprising:
        a spectral image forming circuit that conducts matrix calculation based on a color image signal obtained by the imaging device and forms a spectral image of an arbitrarily selected wavelength range, the spectral image forming circuit being arranged on the processor unit;
        a characteristics information retaining/generating portion having endoscopic characteristics identification information influencing formation of the spectral image, wherein the endoscopic characteristics identification information includes information on at least one of types of color filters of the imaging device and spectral characteristics of the color filters, the characteristics information retaining/generating portion being arranged on the endoscope;
        a characteristics information obtaining portion that obtains the endoscopic characteristics identification information at the characteristics information generating portion, the characteristics information obtaining portion being arranged on the processor unit;
        a storage portion that stores a plurality of matrix data for forming a spectral image corresponding to the endoscopic characteristics identification information; and
        a control portion that reads corresponding matrix data from the storage portion based on the endoscopic characteristics identification information obtained at the characteristics information obtaining portion and allows the spectral image forming circuit to conduct matrix calculation according to the read matrix calculation data;
    wherein the characteristics information obtaining portion obtains information on types of light sources for emitting light illumination from the endoscope end part and selects matrix data according to a type of the light source by referring to a memory unit which stores the information of the types of the light sources by the control portion and which is arranged in the processor unit.

2. The endoscope apparatus according to claim 1, wherein the processor unit recognizes and judges a type of light source, thereby forming a spectral image by using different matrix data which corresponds to both the characteristics of the imaging device or the endoscope and the characteristics information of the light source to conduct matrix calculations on read matrix calculation data.

* * * * *